(12) United States Patent
Shang et al.

(10) Patent No.: US 10,300,295 B2
(45) Date of Patent: May 28, 2019

(54) LIQUID LIGHT CONDUCTING DEVICE USED IN INTERVENTION

(71) Applicant: Hua Shang, Nanjing, Jiangsu (CN)

(72) Inventors: Hua Shang, Nanjing (CN); Zhiwen Wang, Nanjing (CN); Xinjie Lv, Nanjing (CN)

(73) Assignee: Hua Shang, Nanjing, Jiangsu (CN)

( * ) Notice: Subject to any disclaimer, the term of this patent is extended or adjusted under 35 U.S.C. 154(b) by 0 days.

(21) Appl. No.: 16/021,560

(22) Filed: Jun. 28, 2018

(65) Prior Publication Data

US 2019/0015676 A1 Jan. 17, 2019

Related U.S. Application Data

(63) Continuation of application No. PCT/CN2017/093092, filed on Jul. 17, 2017.

(51) Int. Cl.
*A61N 5/06* (2006.01)
*A61M 31/00* (2006.01)

(52) U.S. Cl.
CPC ........... *A61N 5/0601* (2013.01); *A61M 31/00* (2013.01); *A61N 5/062* (2013.01)

(58) Field of Classification Search
CPC .... A61N 5/0601; A61N 5/0603; A61N 5/062; A61N 5/0622; A61N 2005/0602; A61N 2005/0604–2005/0612; A61N 2005/063; A61N 2005/067
See application file for complete search history.

(56) References Cited

U.S. PATENT DOCUMENTS

| 5,169,395 A | 12/1992 | Narciso, Jr. |
| 5,304,171 A * | 4/1994 | Gregory ............... A61B 18/245 385/125 |
| 5,693,049 A | 12/1997 | Mersch |
| 2015/0351644 A1 | 12/2015 | Lee et al. |

FOREIGN PATENT DOCUMENTS

| CN | 106512232 A | 3/2017 |
| CN | 106659393 A | 5/2017 |
| CN | 107213554 A | 9/2017 |
| EP | 0820786 A2 | 1/1998 |

OTHER PUBLICATIONS

Apr. 18, 2018 Written Opinion of the International Searching Authority Issued in International Patent Application No. PCT/CN2017/093092.
Apr. 18, 2018 International Search Report Issued in International Patent Application No. PCT/CN2017/093092.

* cited by examiner

*Primary Examiner* — Eric D. Bertram
(74) *Attorney, Agent, or Firm* — Hauptman Ham, LLP (57) ABSTRACT

A liquid light conducting device used in intervention, comprising a catheter, wherein the inside of the catheter is a cavity, one end of the catheter is provided with a tail sheath, and the other end of the catheter is provided with a liquid-laser coupler which can inject a liquid medium and conduct laser; the tail sheath is provided with an outlet; an inner wall of the catheter is plated with a metal reflecting layer, the liquid medium can be transmitted in the catheter, and laser can be transmitted in the liquid which is coated by the metal reflecting layer and emitted via the tail sheath.

9 Claims, 6 Drawing Sheets

LIQUID LIGHT CONDUCTING DEVICE USED IN INTERVENTION

TECHNICAL FIELD

The present invention relates to the technical field of intervention radiology in the medical field, and in particular to a liquid light conducting device used in intervention.

BACKGROUND ART

In 1953, Seldinger firstly reported a method of intubation through percutaneous femoral artery puncture by using a puncture needle. This closed intubation technology does not block blood flow in the inserted blood vessel (artery or vein) with less bleeding, local complications are reduced to 1.3% from 8%, such that the catheter technology plays an extensive role in diagnostic radiology and interventional radiology, namely, in different fields of surgical radiology. For example, in the external carotid artery intubation which is widely adopted now, before a surgery on malignant tumors at the head and neck region, chemical medicines can be adopted for treatment, the chemical medicines can be directly injected to the tumor site through artery intubation, or a microsphere filled with antitumor medicines can be adopted, the microsphere can be placed in the tumor site through automatic intravenous injection, and then medicines are slowly released, and the curative effect is better. After tumors are confined or reduced, surgical resection may be further performed.

Photodynamic therapy (PDT) is a new technology in disease diagnosis and treatment by utilizing a photodynamic effect. Its function basis is photodynamic effect. This is a photosensitization reaction accompanied by a biological effect with the participation of oxygen molecules. The process is as follows: the photosensitizer absorbed by tissues is stimulated under the irradiation of laser with a certain wavelength, the photosensitizer in an excited state then transfers energy to the surrounding oxygen to generate singlet oxygen with a strong activity, the singlet oxygen performs oxidation reaction with the adjacent biomacromolecules to lead to a cytotoxic effect, further leading to cell damage or even death. Compared with traditional therapies, the photodynamic therapy has the following advantages: 1. Small trauma: by means of optical fiber, endoscope and other intervention technologies, laser can be guided into the deep part in the human body for treatment, thereby avoiding such trauma and pain caused by surgeries including thoracotomy and laparotomy. 2. Selectivity of the treatment area: the PDT therapy is mainly targeted at pathological tissues in the illumination area, has no damage to the bottom of the lesion and surrounding normal tissues, and this selective killing behavior cannot be accomplished by other common methods. Since the photosensitizer is only absorbed and kept by pathological cells, no systemic toxicity exits, the effective light waves are not absorbed by normal tissues, therefore, the treatment is only targeted at pathological tissues and can ensure no damage to normal tissue cells. 3. Effectiveness: injury of blood vessels caused by a photodynamic effect and local ischemia and anoxia of the pathological tissues caused thereby will finally kill the lesions. Meanwhile, since the treatment process is based on a stronger medicine location effect, the medicine location effect is automatically generated at such sites as all the tumors, virus warts, herpes, proliferated blood vessels and macula lutea at the fundus, meanwhile, the immunologic mechanism of the body can be enhanced, thereby preventing relapse or transfer, and ensuring complete eradication with no relapse. 4. No drug resistance and toxic and side effects: since the preparations themselves are not toxic, they will be quickly metabolized after entering the human body, and will not accumulate in the human body, and the body will also not be resistant to the photosensitizer. Therefore, the photodynamic therapy can be used repeatedly. 5. Flexibility: the photodynamic therapy is not limited by other treatment methods, can be independently used and can also be used in combination with other therapies. 6. Noninvasion: the damage to the epithelium tissues and collagen stent of the diseased organs is small, such that the completeness of the appearance and functions of organs can be maintained after the wound surface is healed. During the treatment, no surgery or hospitalization is needed, and the treatment time is short with no trauma and pain.

Since in the photodynamic therapy, major wavelengths are concentrated in the red light wave bands of over 600 nm, the absorption loss of this wave band inside the human body is large, and this wave band generally can only transmit for several millimeters to dozens of millimeters, for some deep seated tumors, no valid photodynamic treatment effect can be achieved; meanwhile, the photosensitizer medicines enter the blood circulation system via intravenous injection, extend all over the human body through blood circulation before reaching the lesion, have a low degree of enrichment at the tumor sites, and have a side effect on normal tissues easily. The present invention provides a liquid light conducting system used in intervention, through the Seldinger artery intubation technology, laser and liquid medicine are introduced into the artery to directly reach the lesion, laser is conducted through the liquid medicine catheter coated by metal, medicine and laser can approach for treatment from the blood vessel channel inside tumors, then photosensitizer and laser can directly act on deep tumors, thereby enhancing the treatment effect and reducing the toxic and side effects.

SUMMARY OF THE INVENTION

In view of this, aiming at the shortcomings that the catheter cannot transmit light energy by adopting the Seldinger artery intubation technology, and the lesion parts inside the human body cannot be approached by adopting the photodynamic therapy, the present invention provides a liquid light conducting device used in intervention, a pipeline through which the light energy and medicine can both be transmitted is formed, medicine and laser can approach for treatment from the blood vessel channel inside tumors, then photosensitizer and laser can directly act on deep tumors, thereby enhancing the treatment effect and reducing the toxic and side effects.

The object of the present invention is realized through the following technical solution:

A liquid light conducting device used in intervention includes a catheter, wherein the inside of the catheter is a cavity, one end of the catheter is provided with a tail sheath, and the other end of the catheter is provided with a liquid-laser coupler which can inject a liquid medium and conduct laser; the tail sheath is provided with an outlet; an inner wall of the catheter is plated with a metal reflecting layer, the liquid medium can be transmitted in the catheter, and laser can be transmitted in the liquid which is coated by the metal reflecting layer and emitted via the tail sheath.

Further, the tail sheath is of a curved structure with a radian, and the tail sheath gradually becomes thinner from the end connected with the catheter to a free end, namely, from a sealed end to the free end, and the tail sheath is of a curved shrinking shape, and the outer diameter becomes smaller and smaller;

Further, the side (namely, the shrinking side or the internal side) in which a concave surface of the curved tail sheath is located is provided with an outlet through which liquid medium can be released and laser can be emitted; and the side (namely, the external side or the extending side) in which the curved tail sheath protrudes outwards is a smooth curved surface.

Further, the tail sheath is made of transparent flexible high polymer materials which can transmit light, for example, transparent high polymers and the like, such that lights can not only be exported from the outlet, but also from the entire transparent tail sheath.

Further, the periphery of the catheter is provided with a hydrophilic layer which is configured to coat the catheter and reduce blood resistance.

Further, the material of the hydrophilic layer is a high polymer, and the high polymer includes teflon.

Further, an outer wall of the catheter is carved with a pattern structure to enhance the flexibility of the catheter, and the pattern structure includes spiral patterns or longitudinal strip-type patterns.

Further, the liquid-laser coupler is provided with a laser inlet, a liquid inlet and a butted opening which is connected with the catheter, and the laser inlet and the butted opening are on the same axis; and the laser inlet is connected with a laser unit which can emit laser.

Further, the opening direction of the liquid inlet is vertical to the axis on which the laser inlet and the butted opening are located.

Further, a laser channel which is capable of transmitting laser to the butted opening is arranged between the laser inlet and the butted opening, and laser then enters the catheter via the butted opening for transmission; and a liquid channel which can transmit the liquid medium to the butted opening is arranged between the liquid inlet and the butted opening, and the liquid medium then enters the catheter via the butted opening.

Further, a transparent medium sealed layer and a lens which can focus laser are arranged on the laser channel along the laser transmission direction.

Further, the catheter is a metal catheter made of metal or a nonmetal catheter made of nonmetal material, and the nonmetal material includes polymers and quartz and the like.

Further, the metal reflecting layer is a silver layer.

Further, the length of the liquid light conducting device is 0.5 m-2 m, the diameter thereof is 0.2 mm-1 mm, the inner diameter of the catheter is 0.25-0.35 mm, and the depth of the patterns carved on the outer wall of the catheter is less than 0.2 mm.

The Present Invention at Least has the Following Beneficial Effects:

The present invention provides a liquid light conducting device used in intervention, through a Seldinger artery intubation technology, laser and liquid medicine are introduced into the artery to directly reach the lesion, the laser is conducted through a liquid medicine catheter which is coated by a metal reflecting layer, and medicine and laser can approach for treatment from the blood vessel channel inside tumors, then photosensitizer and laser can directly act on deep tumors, thereby enhancing the treatment effect and reducing the toxic and side effects. Meanwhile, the whole light conducting device can be bent and rotated, thereby facilitating transmission in the human body.

1. catheter, 2. tail sheath, 3. liquid-laser coupler, 4. hydrophilic layer, 5. cavity, 6. metal reflecting layer, 11. longitudinal strip-type patterns, 21. external side, 22. internal side, 31. laser inlet, 32. liquid inlet, 33. butted opening, 34. laser channel, 35. liquid channel, 100. blood vessel, 101. wall of blood vessel, 221. outlet, 341. transparent medium sealed layer, 342. lens.

DETAILED DESCRIPTION OF THE EMBODIMENTS

A clear and complete description will be given below on the technical solutions of the embodiments in the present invention, and apparently the embodiments described below are only a part but not all of the embodiments of the present invention. A detailed description of the embodiments of the present invention below is not deemed as a limitation on the protection range of the present invention, and only represents the selected embodiments of the present invention. Based upon the embodiments of the present invention, all the other embodiments which can occur to those skilled in the art without any inventive effort shall all fall into the protection scope of the present invention.

Embodiment 1

As shown in FIG. 1 to FIG. 11, a liquid light conducting device used in intervention includes a catheter 1, a tail sheath 2 and a liquid-laser coupler 3, wherein the main body of the liquid light conducting device is the catheter 1 made of metal, for example, the catheter 1 is made of stainless steel materials, the inside of the catheter 1 is a cavity 5 structure, liquid medium and laser can be transmitted in the cavity 5, and the liquid medium may be normal saline, photosensitizer, etc.; an inner wall of the catheter 1 is plated with a metal reflecting layer 6 to reduce the loss of laser when the laser is transmitted in the catheter 1, then liquid medium can be transmitted in the catheter, and laser can be transmitted in the liquid which is coated by the metal reflecting layer 6, and is released to the lesion via the tail sheath 2. The periphery of the catheter is provided with a hydrophilic layer 4 which is configured to coat the catheter, the hydrophilic layer 4 can enhance the blood passing ability of the device and reduce blood resistance; and the material of the hydrophilic layer 4 is high polymers, for example, such high polymer as teflon.

Figure 1:
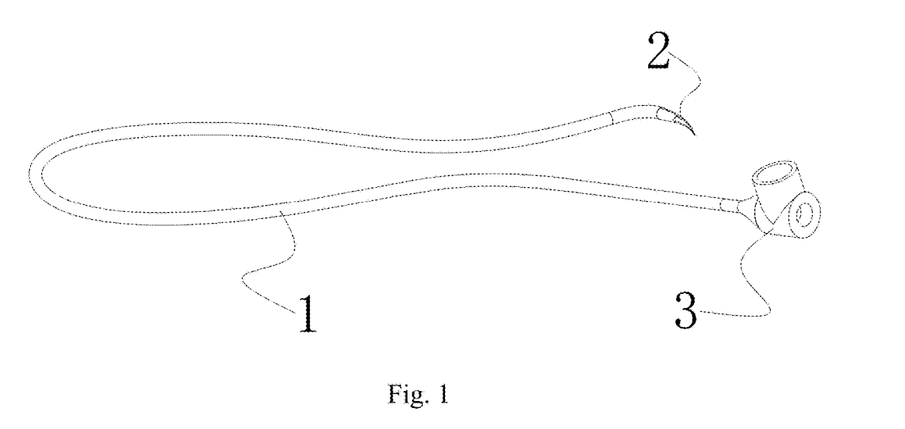
FIG. 1 is a schematic diagram of the overall structure of the liquid light conducting device in the embodiments of the present invention.
Figure 2:
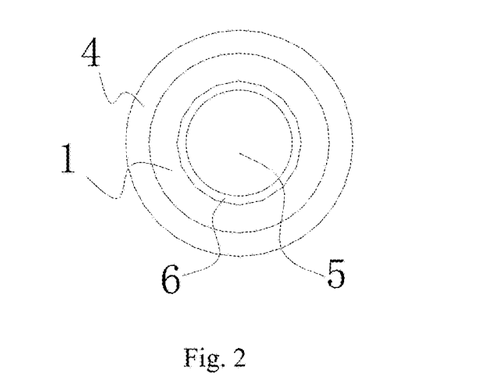
FIG. 2 is a schematic diagram of a cross section of the liquid light conducting device in the embodiments of the present invention.
Figure 3:
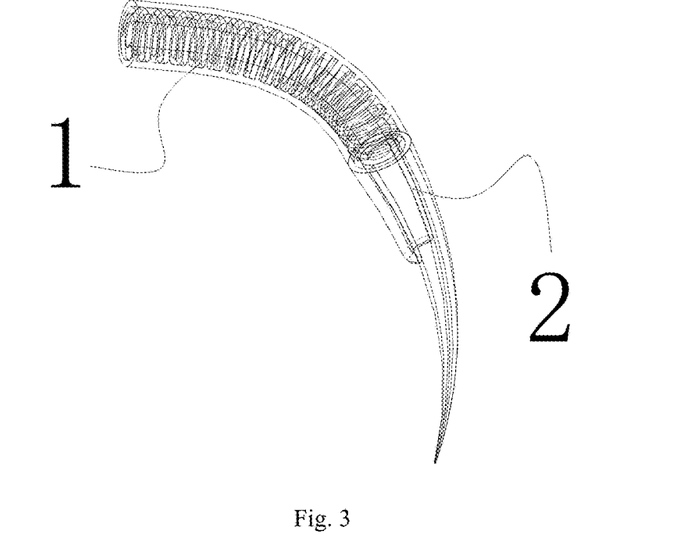
FIG. 3 is a structural schematic diagram of a tail end of the liquid light conducting device in the embodiments of the present invention.
Figure 4:
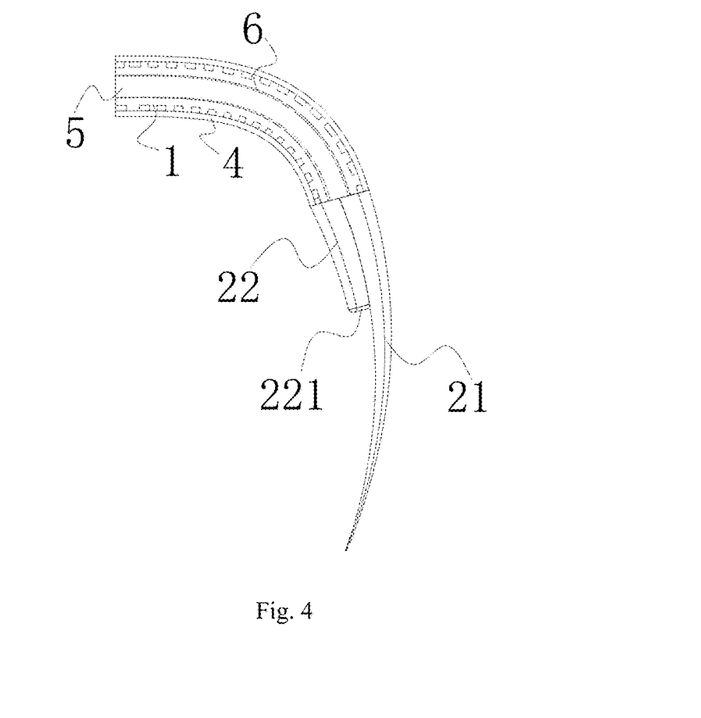
FIG. 4 is a schematic diagram of a cross section of the tail end of the liquid light conducting device in the embodiments of the present invention.

One end of the catheter is provided with a tail sheath 2, and the other end of the catheter is provided with a liquid-laser coupler 3 which can inject a liquid medium and conduct laser;

As shown in FIG. 3 to FIG. 4, the tail sheath 2 is of a curved structure with a radian, its curvature forms about ⅕ to ⅖ of a circle, and the tail sheath 2 gradually becomes thinner from the end connected with the catheter to a free end, namely, from a sealed end to the free end, and the tail sheath is of a curved shrinking shape, and the outer diameter becomes smaller and smaller, then the tail end of the tail sheath 2 is in a shape of a small tip; and the curved shrinking configuration is beneficial for passing through the bifurcation of blood vessels.

The side (namely, the external side 21 or the extending side) in which the curved tail sheath 2 protrudes outwards is a smooth curved surface; the side namely, the shrinking side or the internal side 22) in which a concave surface of the curved tail sheath 2 is located is provided with a notch, namely, an outlet 221 through which liquid medium can be released and part of the laser can also be emitted The tail sheath 2 is made of transparent flexible high polymer materials which can transmit light, for example, transparent high polymers including teflon polymer. The material is flexible and transparent, such that the tail sheath 2 can be deformed on the original basis in the use process, for example, the tail sheath may be subjected to bending deformation, etc. Meanwhile, transparent high polymers enable the laser to be exported not only from the outlet 221, but also from the entire transparent tail sheath 2. The tail end of the light conducting device is provided with a transparent tail sheath which is made of flexible high polymers, thereby being capable of effectively protecting the tail end of the catheter and the inner wall of blood vessels.

Figure 5:
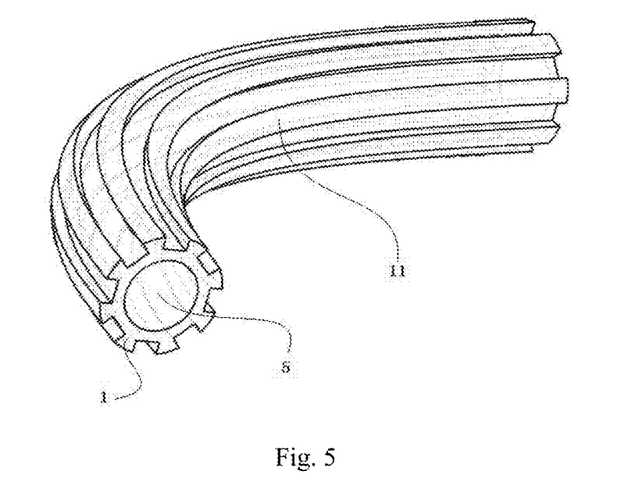
FIG. 5 is a schematic diagram of part of the structure of the catheter containing longitudinal strip-type patterns in the embodiments of the present invention.
Figure 6:
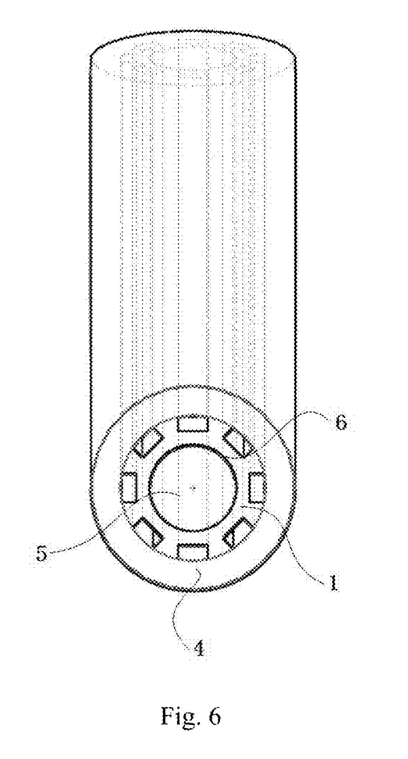
FIG. 6 is a schematic diagram of part of the structure of the light conducting device containing longitudinal strip-type patterns in the embodiments of the present invention.
Figure 7:
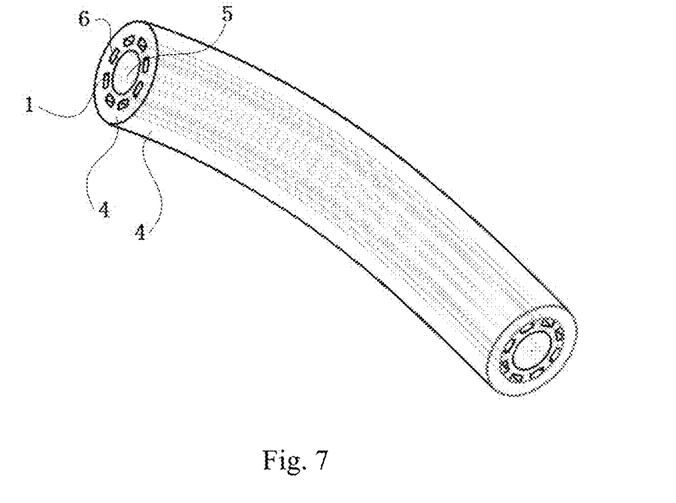
FIG. 7 is a schematic diagram of part of the structure of the light conducting device containing longitudinal strip-type patterns in the embodiments of the present invention.
Figure 8:
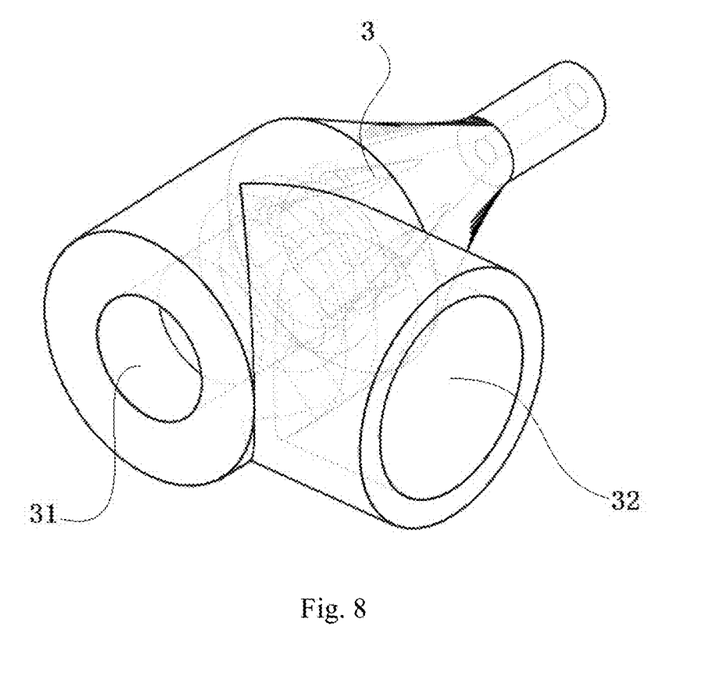
FIG. 8 is a schematic diagram of the three-dimensional structure of the liquid-laser coupler in the embodiments of the present invention.
Figure 9:
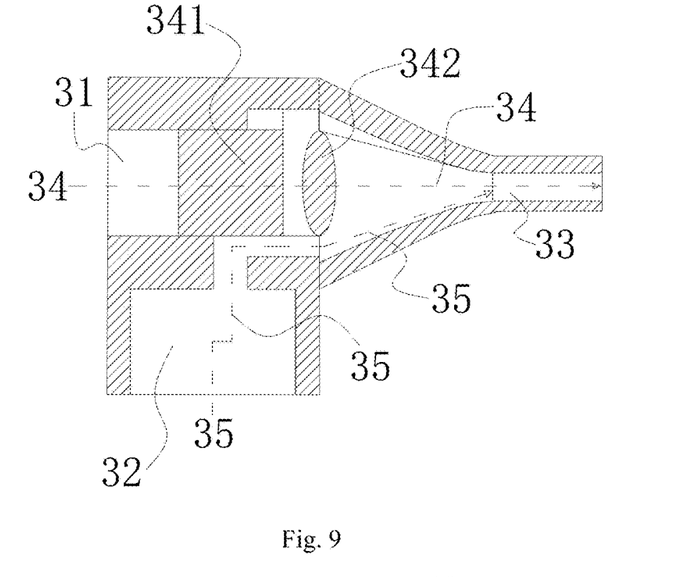
FIG. 9 is a schematic diagram of a cross section of the liquid-laser coupler in the embodiments of the present invention.
Figure 10:
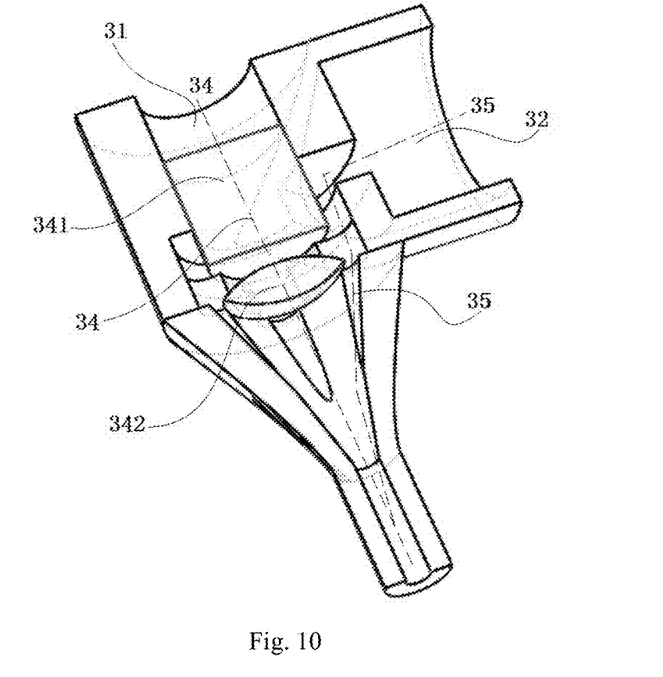
FIG. 10 is a schematic diagram of another cross section of the liquid-laser coupler in the embodiments of the present invention.

As shown in FIG. 3 to FIG. 7, in order to enhance the flexibility or softness of the catheter, the outer wall of the catheter can be carved with patterns through a laser processing mode, namely, a pattern structure can be carved, such that the entire light conducting device can pass through the winding blood vessels in the human body. The pattern structure includes spiral patterns (namely, circular spirals) or longitudinal strip-type patterns 11, the spiral patterns are as shown in FIG. 3 to FIG. 4, and the longitudinal strip-type patterns 11 are as shown in FIG. 5 to FIG. 7, wherein in order to more clearly show the longitudinal strip-type patterns 11, FIG. 5 only shows the structure of the catheter 1, with other structural layers being omitted.

Figure 11:
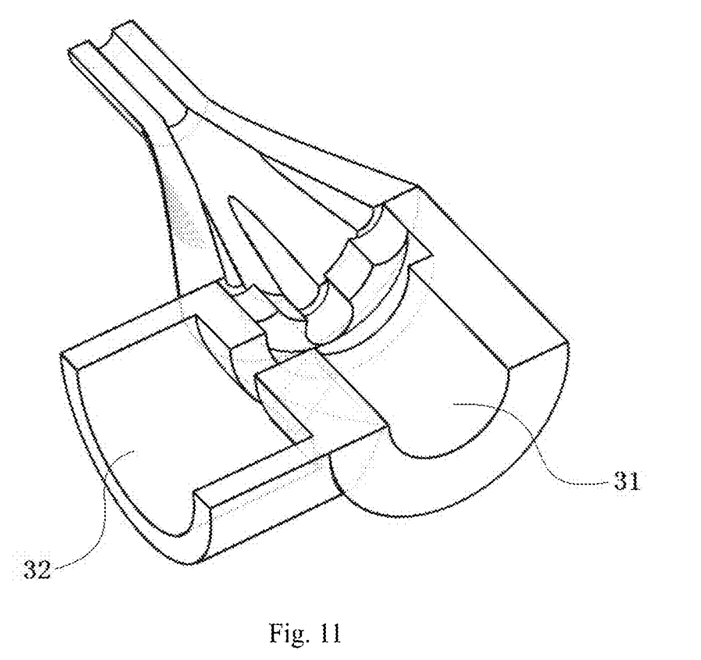
FIG. 11 is a schematic diagram of a cross section of the liquid-laser coupler in the embodiments of the present invention with part of the structure being omitted.

As shown in FIG. 8 to FIG. 11, a transparent medium sealed layer 341 and a lens 342 are omitted in. FIG. 11, the liquid-laser coupler 3 is arranged at the outermost end of the liquid light conducting device, namely, at the end which is left outside the human body, the liquid-laser coupler 3 is provided with a laser inlet 31, a liquid inlet 32 and a butted opening 33 which is connected with the catheter, and the laser inlet 31 and the butted opening 33 are on the same axis, thereby facilitating the transmission of light in a straight line.

The laser inlet 31 is connected with the laser unit which is capable of emitting laser, a laser channel 34 which is capable of transmitting laser to the butted opening 33 is arranged between the laser inlet 31 and the butted opening 33, and laser then enters the catheter via the butted opening 33 for transmission; the laser channel 34 is a straight-line channel, thereby facilitating the transmission of light; a. transparent medium sealed layer 341 which can seal the laser inlet 31 and a lens 342 which can focus laser are arranged on the laser channel 34 along the laser transmission direction. Then during use, the laser unit emits laser, laser enters the laser channel 34, then passes through the transparent medium sealed layer 341 and is condensed by the lens 342, then is transmitted to the cavity 5 of the catheter for transmission, and finally penetrates out of the liquid light conducting device from the tail sheath 2. The materials of the lens 342 and the transparent medium sealed layer 341 can be K9 glass, resin (diallyl 2,2'-oxydiethyl dicarbonate), etc. The transparent medium sealed layer 341 can isolate the liquid and laser channel, thereby preventing liquid from entering the laser channel and ensuring light transmittance.

Liquid medium is introduced into the liquid inlet 32 from the side face, namely, the opening direction of the liquid inlet 32 is vertical to the axis on which the laser inlet 31 and the butted opening 33 are located. A liquid channel 35 which can transmit the liquid medium to the butted opening 33 is arranged between the liquid inlet 32 and the butted opening 33, the liquid channel 35 is a microchannel, liquid medium is introduced from the liquid inlet 32, and then enters the catheter via the liquid channel 35 for transmission.

The laser inlet 31 and the liquid inlet 32 do not influence each other, and they can work independently or work simultaneously. Liquid and laser can be introduced into the catheter simultaneously via the liquid-laser coupler 3.

The refractive index of the liquid medium in the catheter is about 1.33.

The length of the liquid light conducting device is 0.5 m-2 m, the diameter thereof is 0.2 mm-1 mm, the inner diameter of the catheter is 0.25-0.35 mm, the whole catheter can be bent and rotated, and the depth of the patterns carved on the outer wall of the catheter is less than 0.2 mm.

As a further preferred embodiment, the metal reflecting layer 6 is a silver reflecting layer, namely, a silver film is plated on the inner wall of the catheter.

As a further preferred embodiment, the surface on which the notch or outlet 221 on the tail sheath 2 is located is vertical to the tangent line of the curved tail sheath at the notch or outlet 221.

Embodiment 2

For the catheter in Embodiment 1, a nonmetal catheter can also be made from nonmetal materials, for example, the catheter can be made from polymers or quartz, etc.

Figure 12:
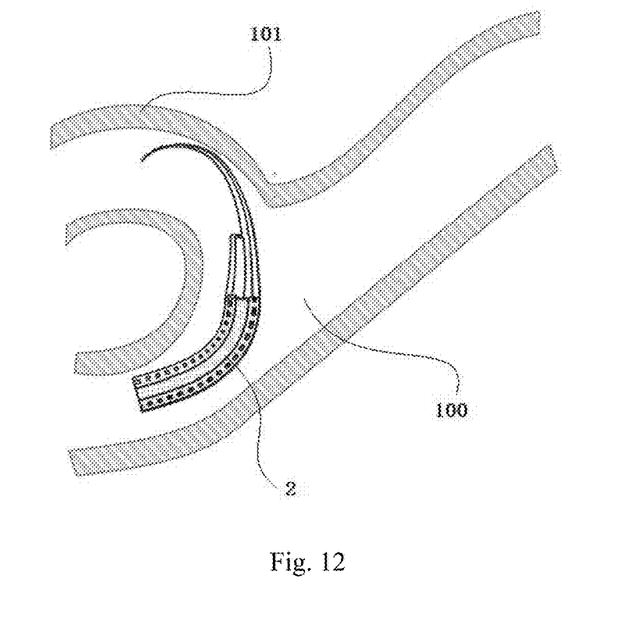
FIG. 12 is a schematic diagram showing that the tail sheath is located inside the blood vessel in the embodiments of the present invention.

During specific implementation, 306 stainless steel catheter with an inner diameter of 0.3 mm and an outer diameter of 0.5 mm is taken as a main body, the inner wall is plated with a silver film, the outer wall is carved with annular spiral patterns, and the carved thickness is less than 0.2 mm; the refractive index of liquid inside the cavity 5 of the catheter is 1.33, and the laser is transmitted to the tail sheath under the reflection of liquid and the inner wall of the catheter. The tail sheath is made of transparent heat-shrinkable polymer materials to closely wrap the outer wall of the catheter, the tail sheath bends and gradually becomes thin, and the tail sheath and the catheter can be molded in one step; the diameter of the tip end of the tail sheath, namely, the outermost free end, can be the same as or even less than the diameter of the cavity 5 inside the catheter, and this is specifically determined based on actual conditions; the tail sheath of such a structure plays a role of protecting the catheter and blood vessels; the tail sheath is transparent, can be penetrated by the laser and is provided with an outlet 221 which is used for outputting medicine. The tail sheath 2 is in a C shape when viewed from its entirety, thereby being beneficial for selecting directional signals in the blood vessel, and selecting directions through rotating when confronting with bifurcations of blood vessels 100, the flexible tail sheath 2 will be subjected to proper bending deformation on the original basis to play a guiding role on the whole device, as shown in FIG. 12, and the grey dash area in the figure is the blood vessel wall 101. The liquid-laser coupler 3 serves as a connecting end in vitro, the laser inlet of the liquid-laser coupler 3 is provided with a transparent medium sealed layer which is configured to seal liquid to transmit laser, and focusing and coupling are performed via the lens 342; and the liquid is introduced into the catheter via the microchannel on the side face.

During specific use, the whole liquid light conducting device can be bent and rotated, and through the Seldinger artery intubation technology laser and liquid medicine enter the blood vessel to approach the lesion under the guidance of the tail sheath. Specifically, in the treatment of photodynamic tumor inside blood vessels, for example, when introducing photosensitizer and red laser into blood vessels in liver tumors, firstly, the liquid light conducting device is connected to a medicine injection device and a red laser unit, percutaneous puncture is performed on the blood vessel, and the optical fiber catheter is inserted into the lesion under the guidance of clinical imaging. The photosensitizer medicine enters the catheter via the liquid channel 35 for conduction, and is finally introduced to the tumor site via the outlet of the tail sheath, the red laser is transmitted under the reflection of liquid and the inner wall of the catheter, and then irradiates on the tumor which has been injected with a photosensitive medicine via the transparent tail sheath, such that the photosensitive medicine inside the tumor is subjected to photochemical reaction to generate singlet oxygen and further lead to necrosis and apoptosis of the tumor, thereby achieving the aim of treating tumors.

What is described above is merely preferred embodiments of the present invention, rather than limiting the present invention. For those skilled in the art, various modifications and transformations can be made to the present invention. Any modification, equivalent substitution and improvement made within the spirit and principle of the present invention shall all fall within the protection scope of the present invention.

The invention claimed is:

1. A liquid light conducting device used in intervention, comprising a catheter, wherein the inside of the catheter is a cavity, one end of the catheter is provided with a tail sheath, and the other end of the catheter is provided with a liquid-laser coupler which can inject a liquid medium and conduct laser;

the tail sheath is provided with an outlet;

an inner wall of the catheter is plated with a metal reflecting layer, the liquid medium can be transmitted in the catheter, and laser can be transmitted in the liquid which is coated by the metal reflecting layer and emitted via the tail sheath;

the tail sheath is of a curved structure with a radian, and the tail sheath gradually becomes thinner from the end connected with the catheter to a free end;

the side in which a concave surface of the curved tail sheath is located is provided with an outlet through which liquid medium can be released and laser can be emitted; and the side in which the curved tail sheath protrudes outwards is a smooth curved surface.

2. The liquid light conducting device used in intervention of claim 1, wherein the periphery of the catheter is provided with a hydrophilic layer which is configured to coat the catheter and reduce blood resistance.

3. The liquid light conducting device used in intervention of claim 2, wherein the tail sheath is made of transparent flexible high polymer materials which can transmit light, such that laser can be exported from the entire transparent tail sheath; and the material of the hydrophilic layer is a high polymer, and the high polymer comprises teflon.

4. The liquid light conducting device used in intervention of claim 3, wherein an outer wall of the catheter is carved with a pattern structure to enhance the flexibility of the catheter, and the pattern structure comprises spiral patterns or longitudinal strip-type patterns.

5. The liquid light conducting device used in intervention of claim 4, wherein the liquid-laser coupler is provided with a laser inlet, a liquid inlet and a butted opening which is connected with the catheter, and the laser inlet and the butted opening are on the same axis; and the laser inlet is connected with a laser unit which can emit laser.

6. The liquid light conducting device used in intervention of claim 5, wherein a laser channel which is capable of transmitting laser to the butted opening is arranged between the laser inlet and the butted opening, and laser then enters the catheter via the butted opening for transmission; and a liquid channel which can transmit the liquid medium to the butted opening is arranged between the liquid inlet and the butted opening, and the liquid medium then enters the catheter via the butted opening.

7. The liquid light conducting device used in intervention of claim 6, wherein a transparent medium sealed layer and a lens which can focus laser are arranged on the laser channel along the laser transmission direction.

8. The liquid light conducting device used in intervention of claim 7, wherein the opening direction of the liquid inlet is vertical to the axis on which the laser inlet and the butted opening are located;

the catheter is a metal catheter made of metal or a nonmetal catheter made of nonmetal material, and the nonmetal material comprises polymers and quartz; and the metal reflecting layer is a silver layer.

9. The liquid light conducting device used in intervention of claim 4, wherein the length of the liquid light conducting device is 0.5 m-2 m, the diameter thereof is 0.2 mm-1 mm, the inner diameter of the catheter is 0.25-0.35 mm, and a depth of the patterns carved on the outer wall of the catheter is less than 0.2 mm.

* * * * *